(12) United States Patent
Thornton et al.

(10) Patent No.: US 10,888,898 B2
(45) Date of Patent: Jan. 12, 2021

(54) SHIELDED ULTRASOUND TRANSDUCER AND IMAGING SYSTEM EMPLOYING THE SAME

(71) Applicant: ENDRA Life Sciences Inc., Ann Arbor, MI (US)

(72) Inventors: Michael M. Thornton, London (CA); Stanley Emil Jelic, Ann Arbor, MI (US)

(73) Assignee: ENDRA Life Sciences Inc., Ann Arbor, MI (US)

( * ) Notice: Subject to any disclaimer, the term of this patent is extended or adjusted under 35 U.S.C. 154(b) by 557 days.

(21) Appl. No.: 15/918,392

(22) Filed: Mar. 12, 2018

(65) Prior Publication Data

US 2019/0275562 A1  Sep. 12, 2019

(51) Int. Cl.
| | |
|---|---|
| *H01L 41/04* | (2006.01) |
| *B06B 1/06* | (2006.01) |
| *G01N 29/24* | (2006.01) |
| *A61B 8/00* | (2006.01) |
| *G01N 29/32* | (2006.01) |

(52) U.S. Cl.
CPC .......... *B06B 1/0662* (2013.01); *A61B 8/4483* (2013.01); *G01N 29/2437* (2013.01); *G01N 29/32* (2013.01); *B06B 2201/76* (2013.01)

(58) Field of Classification Search
CPC .............. B06B 1/0662; B06B 2201/76; G01N 29/2437; G01N 29/32; A61B 8/4483
USPC .................................. 310/328, 334, 365, 366
See application file for complete search history.

(56) References Cited

U.S. PATENT DOCUMENTS

| | | | |
|---|---|---|---|
| 6,536,275 B1* | 3/2003 | Durkee ............... | G01F 23/2962 73/290 V |
| 10,328,642 B2* | 6/2019 | Deaville ................. | B29C 70/32 |
| 2003/0178916 A1* | 9/2003 | Ingram ................ | G10K 11/006 310/328 |
| 2014/0219063 A1* | 8/2014 | Hajati ...................... | B25J 9/104 367/157 |
| 2018/0271372 A1* | 9/2018 | Lee ...................... | A61B 8/4416 |

FOREIGN PATENT DOCUMENTS

| | | | | |
|---|---|---|---|---|
| GB | 2469867 A | * | 3/2010 | ............. G01N 11/08 |
| WO | WO-2013058297 A1 | * | 4/2013 | ............. H04R 17/00 |

* cited by examiner

*Primary Examiner* — Thomas M Dougherty
(74) *Attorney, Agent, or Firm* — Stanley E. Jelic

(57) ABSTRACT

An ultrasound transducer with at least one piezoelectric element configured to convert received acoustic signals into an electric potential, a shield connectable to ground and overlying the at least one piezoelectric element through which the acoustic signals pass before being received by the at least one piezoelectric element, the shield having acoustic conductivity and electrical attenuation characteristics that enable the acoustic signals to propagate therethrough while reducing a 100 volt per centimeter electric field to below a threshold level so that the piezoelectric element is exposed to a threshold electrical potential at least less than or equal to 10 µV, and a housing accommodating the at least one piezoelectric element and shield.

16 Claims, 7 Drawing Sheets

SHIELDED ULTRASOUND TRANSDUCER AND IMAGING SYSTEM EMPLOYING THE SAME

FIELD

The subject application relates generally to ultrasound transducers and in particular, to a shielded ultrasound transducer and to an imaging system employing the same.

BACKGROUND

Medical imaging systems that employ ultrasound are known in the art. For example, medical ultrasound imaging systems typically comprise an ultrasound probe having an ultrasound transducer encased in a plastic housing of the ultrasound probe. The ultrasound transducer may comprise a single piezoelectric element or an array of piezoelectric elements. An ultrasound machine provides short and strong electrical pulses to the ultrasound probe that drive the piezoelectric element(s) of the ultrasound transducer at the desired frequency, typically in the range of 1 MHz to 18 MHz. In response, the ultrasound transducer outputs a sound (acoustic) wave that is focused into an arc-shape by the ultrasound probe, either by a lens or by beamshaping, and is directed into the subject or patient being imaged. The sound wave entering the subject is then partially reflected from the layers of different tissues within the subject or scattered by structures within the subject and some of the reflections return to and enter the ultrasound probe. The returning, sound wave reflections in turn vibrate the piezoelectric element(s) of the ultrasound transducer causing the piezoelectric element(s) to convert the vibrations into an electrical potential. In response to the electrical potential, electrical pulses are conveyed to an ultrasound scanner that processes and, transforms the electrical pulses into a digital image.

Thermoacoustic imaging systems also typically comprise an ultrasound probe having an ultrasound transducer encased in a plastic housing of the ultrasound probe. The ultrasound transducer may comprise a single piezoelectric element or an array of piezoelectric elements. An electromagnetic (EM) transmitter or power source supplies energy at the appropriate power, frequency, and pulse shape to an EM applicator that in turn transmits pulses of EM energy into the subject or patient being imaged. The EM energy pulses transmitted into the subject stimulate the generation of thermoacoustic signals within the subject or patient that are received by the ultrasound probe. The received thermoacoustic signals in turn vibrate the piezoelectric elements) of the ultrasound transducer causing the piezoelectric element(s) to convert the vibrations into an electrical potential. In response to the electrical potential, electrical pulses are conveyed to a data acquisition system that processes and transforms the electrical pulses into a digital image.

Medical imaging systems that employ ultrasound such as those described above are regulated by strict guidelines for radiated emissions to prevent interference, such as electromagnetic interference (EMI) and/or radio-frequency interference (RFI), with other medical equipment and to preserve the integrity of acquired images for patient diagnosis. As will be appreciated, radio frequency (RF) and EM emissions from medical imaging systems that employ ultrasound may cause interference with the operation of other sensitive medical equipment. Also RF and EM emissions from other medical equipment may cause interference with the medical imaging systems that employ ultrasound, thereby affecting the quality of signal measurements and resultant acquired images. Accordingly, it is desirable to shield the electronics and probes of medical imaging systems to prevent EM and RF emissions from causing unwanted interference thereby ensuring adequate imaging.

The need to shield the electronics and probes of medical images systems to prevent EM and/or RF emissions from causing interference is more pronounced in thermoacoustic imaging systems as the effects of EMI and/or RFI are increased. This is due to the fact that the EM applicator of the thermoacoustic imaging system, during use, emits, high-energy EM pulses, which can typically generate a significant electric field in the order of 100 V/cm.

In such, a high electric field environment, providing insufficient shielding for the electronics and probes of the thermoacoustic imaging system may result in a number of problems. For example, the high electric field may induce a signal on the ultrasound transducer that could interfere with measured acoustic signals, resulting in inaccurate imaging. The high-energy EM pulses also may induce the ultrasound transducer to transmit a signal that could interfere with the thermoacoustic signals generated within the subject. Further, the high electric field may damage electronics used to acquire the thermoacoustic images.

Not surprising, ultrasound transducers that attenuate EM and/or RF emissions have been considered. For example, an existing shielded ultrasound transducer 100 having a single piezoelectric element is shown in FIGS. 1A and 1B. The ultrasound transducer 100 comprises a generally cylindrical housing 102 formed of a metallic material that is open at one end. A piezoelectric 104 element having a front surface 104a and a rear surface 104b is positioned within the housing 102 adjacent the open end of the housing. A potential electrode 106 overlies and covers the rear surface 104b of the piezoelectric element 104. A backing block 108 is positioned within the housing 102 behind the potential electrode 106 and the piezoelectric element 104 and acts to prevent excessive vibration of the piezoelectric element. An acoustic insulator 110 fills the void within the housing 102 and surrounds the backing block 108 and the piezoelectric element 104 to electrically insulate the piezoelectric element from the housing and to protect the piezoelectric element 104 from transient signals. A shield 112 covers the open end of the housing 102. The shield 112 comprises a thin membrane 114 having an outer facing surface 116 and an inner surface 118 facing the piezoelectric element, and a metal ground electrode 120 on the inner surface 118 of the thin membrane 114 and overlying and covering the front surface 104a of the piezoelectric element 104. The ground electrode 120 is electrically coupled to ground G via, a ground wire 122 and is sufficiently thin to limit its acoustic signal attenuation losses. A cable 124 that is electrically connected to the potential electrode 106 extends from the housing 102 and is used to communicate electrical pulses to downstream equipment 126 for processing, transformation and image generation.

During operation, when thermoacoustic signals or ultrasound sound wave reflections (for ease of description, hereinafter referred to as "acoustic signals") impinge on the ultrasound transducer 100, the acoustic signals pass through the thin membrane 114 and ground electrode 120 with some attenuation and impinge on the piezoelectric element 104. In response to the force of the acoustic signals on the piezoelectric element 104 the piezoelectric element 104 vibrates causing the piezoelectric element to convert the vibrations into an electrical potential that appears on the potential electrode 106. In response to the electrical potential, electrical pulses are conveyed via the cable 124 to the downstream equipment 126 for processing and transformation allowing the electrical pulses to be converted into a digital image.

As mentioned above, the ultrasound transducer 100 may be subjected to EM and/or RF emissions during operation. The metallic material housing 102 acts as a shield to inhibit EM and/or RF emissions from entering the housing from locations other than its open end covered by the shield 112. EM and/or RF emissions that impinge on the shield 112 pass through the thin membrane 114 to the ground electrode 120 where some of the EM and/or RF emissions are shunted to ground G via the ground wire 122 thereby providing the piezoelectric element 104 with some shielding, from the EM and/or RF emissions. EM and/or RF emissions that are not shunted to ground G via the ground electrode 120 and ground wire 122 pass through the ground electrode 120 and impinge on the piezoelectric element 104. Although the shield 112 acts to shunt EM and/or RF emissions to ground, it has been found that in high EMI and/or RFI environments, the effectiveness of the shield 112 is limited resulting in EM and/or RF emissions impinging on the piezoelectric element 104 that are sufficient in magnitude to lead to the problems discussed above.

Those of skill in the art will appreciate that if the ultrasound transducer comprises an array of piezoelectric elements, each piezoelectric element is shielded from EM and/or RF emissions either by a single shunted ground electrode overlying the entire piezoelectric element array or by multiple shunted ground electrodes overlying individual ones or groups of piezoelectric elements.

Other shielded ultrasound transducers have also been considered to protect them from EM and/or RF emissions. For example, thin metal layers positioned on or around the focusing lens of the ultrasound probe have been employed to protect the electrical components of the ultrasound transducer and the cable from EM and/or RF emissions. Unfortunately, as the attenuation losses for metal are severe, no more than a few layers of thin metal can be used to protect the electrical components of the ultrasound transducer and cable from EMI and/or RFI limiting their effectiveness; otherwise the acoustic signal losses will be too severe for adequate imaging.

Although shielded ultrasound transducers have been considered, improvements are desired, particularly in imaging system environments such as thermoacoustic imaging where EM and/or RF emissions are pronounced. It is therefore an object at least to provide a novel shielded ultrasound transducer and an imaging system employing the same.

SUMMARY

It should be appreciated that this summary is provided to introduce a selection of concepts in a simplified form that are further described below in the detailed description. This summary is not intended to be used to limit the scope of the claimed subject matter.

In one aspect there is provided an ultrasound transducer comprising at least one piezoelectric element configured to convert received acoustic signals into an electric potential; a shield connectable to ground and overlying the at least one piezoelectric element through which the acoustic signals pass before being received by the at least one piezoelectric element, the shield having acoustic conductivity and electrical attenuation characteristics that enable the acoustic signals to propagate therethrough while reducing a 100 volt per centimeter electric field to below a threshold level so, that the piezoelectric element is exposed to a threshold electrical potential less than or equal to 10 µV; and a housing accommodating the at least one piezoelectric element and shield.

In one embodiment, the threshold electrical potential is less than or, equal to 5 µV.

In one embodiment, the threshold electrical potential is less than or equal to 1 µV.

In one embodiment, the shield is formed of an elastic conductive material, the elastic conductive material comprising a matrix formed of a bulk polymer material with metal particles or metal ions generally uniformly dispersed therein.

In one embodiment, the ultrasound transducer further comprises one or more conductors electrically connecting the shield to ground.

In one embodiment, the shield comprises a membrane overlying an open end of the housing and gel material interposed between the membrane and the at least one piezoelectric element.

In one embodiment, the shield comprises a cap on an open end of the housing enclosing a void and gel material accommodated by the void.

In another aspect there is provided an ultrasound transducer comprising: at least one piezoelectric element configured to convert received acoustic signals into an electric potential; a housing accommodating the at least one piezoelectric element; a cover on an end of the housing and overlying the at least one piezoelectric element through which the acoustic signals pass before being received by the at least one piezoelectric element; and a cage-like structure formed of electrically conductive material surrounding the housing and being electrically insulated therefrom, the cage-like structure configured to enable the acoustic signals to propagate therethrough and configured to inhibit electromagnetic interference (EMI) and/or radio frequency interference (RFI) from passing therethrough.

In one embodiment, the cage-like structure is electrically insulated from the housing by one or more insulators extending between the cage-like structure and the housing.

In one embodiment, the cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 10 µV.

In one embodiment, the cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 5 µV.

In one embodiment, the cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 1 µV.

BRIEF DESCRIPTION OF THE DRAWINGS

Embodiments will now be described more fully with reference to the accompanying drawings in which.

DETAILED DESCRIPTION

Figure 1A:
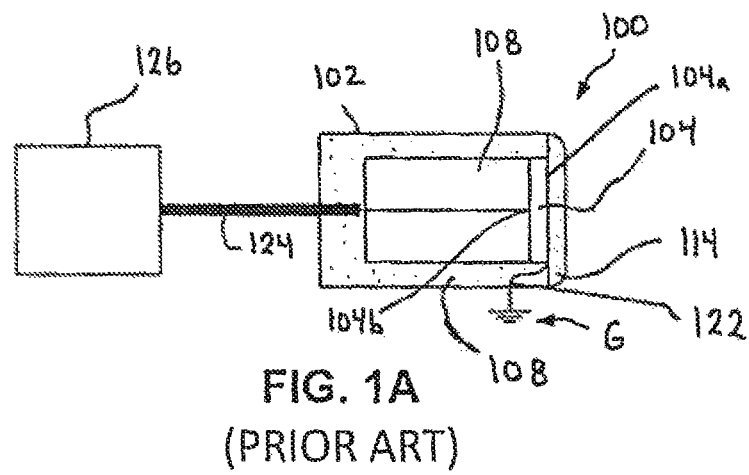
FIG. 1A is a schematic diagram of a prior art ultrasound transducer.
Figure 1B:
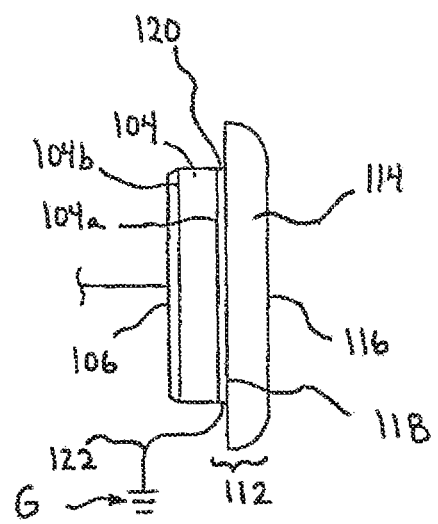
FIG. 1B is a partial side view of the prior art ultrasound transducer of FIG. 1A.

The foregoing summary, as well as the following detailed description of certain examples will be better understood when read in conjunction with the appended, drawings. As used herein, an element or feature introduced in the singular and preceded by the word "a" or "an" should be understood as not necessarily excluding the plural of the elements or features. Further, references to "one example" or "one embodiment" are, not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including by not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientation depicted in the figures.

In the following, ultrasound transducers are described that are particularly suited, for use in high EMI and/or RFI environments such as in thermoacoustic imaging systems where electrical fields in the order of 100 V/cm are generated in response to high energy EM pulses emitted by the EM applicator of the thermoacoustic imaging system. The ultrasound transducers make use of a shield that effectively attenuates high EM and/or RF emissions to inhibit the piezoelectric element(s) of the ultrasound transducers from being subjected, to electric potentials that can adversely impact imaging while minimally attenuating received acoustic signals to ensure adequate imaging. As will be appreciated, for better imaging results it is desired that the ultrasound transducers exhibit little or no acoustic signal attenuation to maximize the amplitude of acoustic signals impinging on the piezoelectric element(s), and exhibit maximum electromagnetic interference (EMI) and/or radio frequency interference (RFI) attenuation to limit exposure of the piezoelectric element(s) to EM and/or RF emissions.

Before describing exemplary ultrasound transducers, a background discussion of acoustic attenuation, the need to maximize acoustic signal amplitude and the need to provide sufficient shielding to maximize EMI and/or RFI attenuation in high EMI and/or RFI medical ultrasound imaging environments is provided.

As a sound wave travels through a medium, the intensity of the sound wave diminishes with respect to distance. In ideal materials, the sound pressure (sound wave amplitude) is only reduced by the spreading of the sound wave. Natural materials, however, scatter and absorb portions of the sound wave thereby weakening the sound pressure as the sound wave travels therethrough. As will be appreciated, scattering is the reflection of the sound wave in directions other than the original direction of propagation. Absorption is the conversion of sound to other forms of energy. Attenuation is the combined effect of scattering and absorption. Ultrasound attenuation is the decay rate of an ultrasound acoustic signal as, it propagates through a material.

The change of amplitude of a decaying wave is expressed by Equation 1:

$$A = A_0 e^{-\alpha z} \qquad [1]$$

where $A_0$ is the unattenuated amplitude of the propagating wave at a particular location, A is the reduced, amplitude after the propagating wave has traveled a distance z from the particular location (measured in nepers per meter (Np/m), $\alpha$ is the attenuation coefficient of the propagating wave, and e is Napier's constant. The amplitude A of the decaying wave calculated using Equation 1 and measured in Np/m can be converted to decibels per meter (dB/m) by dividing it by 0.1151.

As is known, attenuation is proportional to the square of sound frequency. Values of attenuation are often provided for a single frequency. Alternatively, an attenuation value averaged over many frequencies may be provided. The actual value of the attenuation coefficient for a given material is highly dependent on the manner in which the material was manufactured. As such, a reliable value of attenuation can only be obtained for a given material experimentally.

In the case of an ultrasound acoustic signal, the attenuation coefficient may be determined by evaluating multiple backwall reflections seen in typical A-scan ultrasound. In this case, the number of decibels (dB) between two adjacent ultrasound acoustic signals is determined and divided by the time interval between the two adjacent ultrasound acoustic signals. The resultant value represents the attenuation coefficient in decibels (dB) per unit time $U_t$. Equation 2 shows how to convert this resultant value to nepers/m:

$$\alpha = [0.1151/v]U_t \quad [2]$$

The attenuation of EM and/or RF emissions can be estimated theoretically and with experimental data. For theoretical estimates, attenuation is estimated by calculating the absorption loss in grounded media through which EM and/or RF emissions travel. The theoretical absorption loss A (in decibels dB) is expressed by Equation 3:

$$A = 3.338t(\mu\sigma F)0.5 \quad [3]$$

where μ is the relative permeability, a is the relative conductivity, and F is the frequency (MHz).

Figure 2:
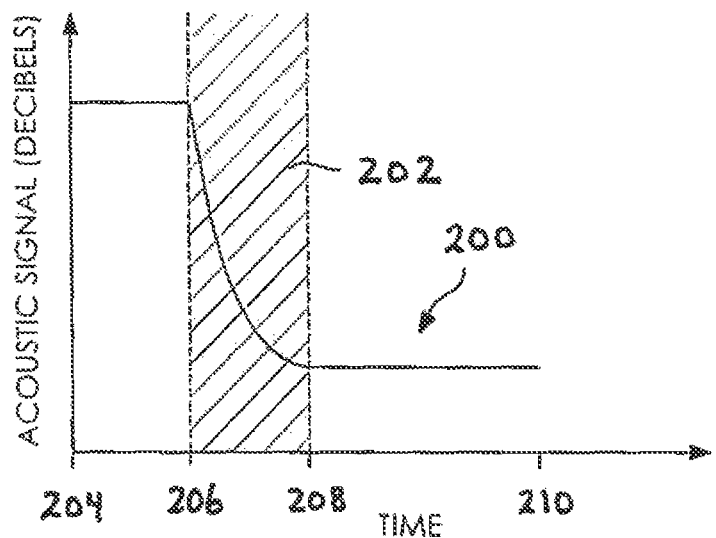
FIG. 2 is an acoustic attenuation curve of a propagating acoustic signal that passes through an acoustic conductor under ideal conditions.

FIG. 2 shows an acoustic attenuation curve 200 of a propagating acoustic signal that passes through an acoustic conductor 202 under ideal conditions. As can be seen, the acoustic signal begins propagating at time 204 with virtually no attenuation until time 206 at which time the acoustic signal enters the acoustic conductor 202. During time 206 to 208, the acoustic signal propagates through the acoustic conductor 202 and is subject to attenuation where the acoustic signal loses strength or amplitude (typically measured in decibels). At time 208, the acoustic signal exits the acoustic conductor 202 and continues, propagating to time 210 with virtually no further attenuation.

Figure 3:
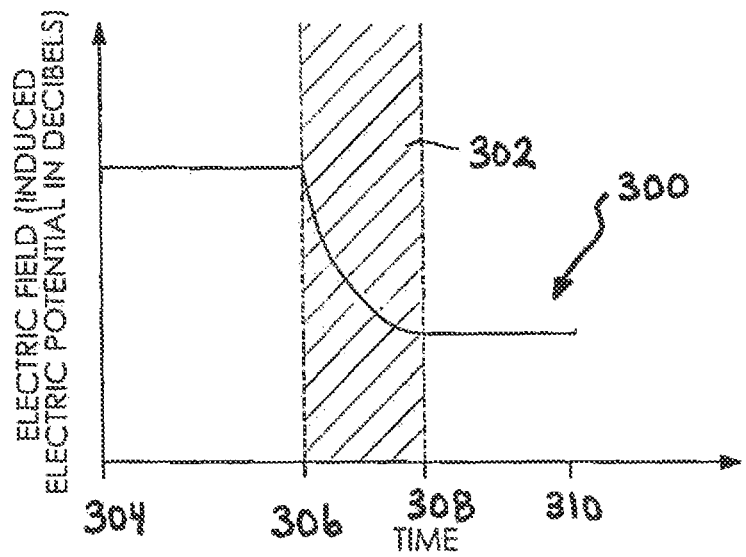
FIG. 3 is an RF attenuation curve of a propagating electric field that passes through an electrical attenuator under ideal conditions.

FIG. 3 shows an RF attenuation curve 300 of an electric field propagating through an electrical attenuator 302. As can be seen, the electric field begins propagating at time 304 with virtually no attenuation until time 306 at which time the electric field enters the electrical attenuator 302. During, time 306 to 308, the electric field propagates through the electrical attenuator 302 and is subject to attenuation where the electric field loses strength or amplitude (typically measured in volts). At time 308, the electric field exits the electrical attenuator 302 and continues propagating to time 310 with virtually no further attenuation.

Figure 4:
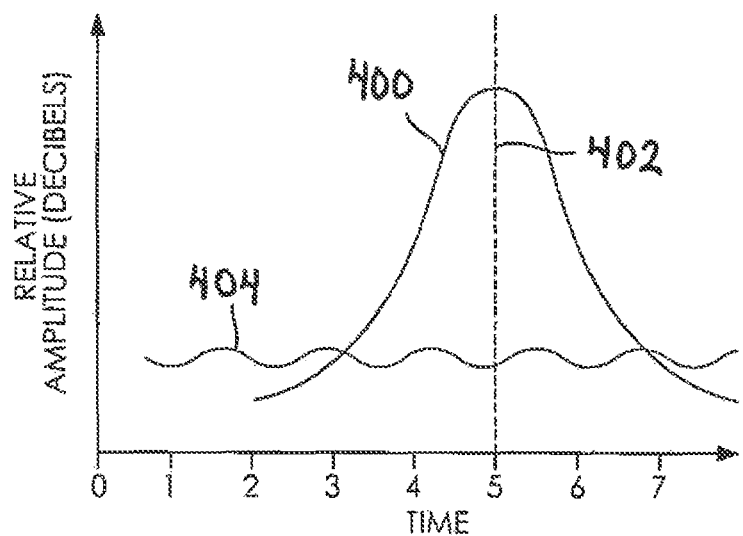
FIG. 4. is a typical ultrasound signal overlaid with acoustic noise.

FIG. 4 shows a typical ultrasound signal 400 having a centerline 402 at about 5 MHz overlaid with acoustic noise/signal interference 404 that could be caused by EMI/RFI.

Figure 5:
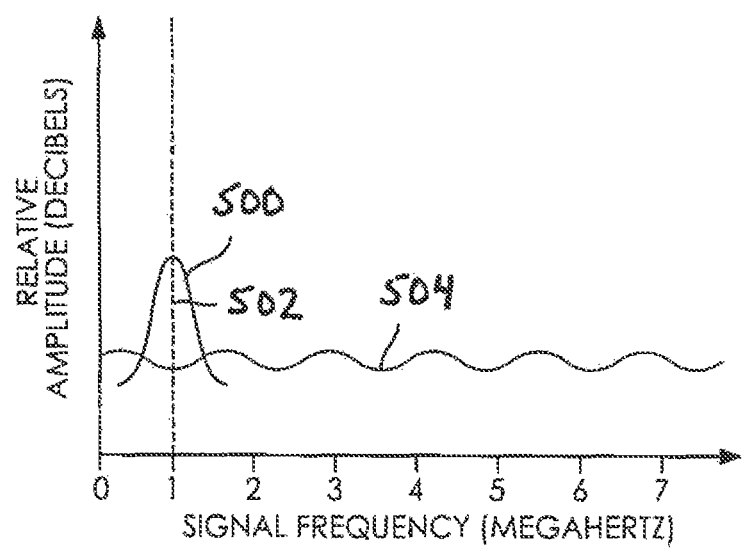
FIG. 5. is a typical thermoacoustic signal overlaid with acoustic noise.

FIG. 5 shows a typical thermoacoustic signal 500 having a centerline 502 at about 1 MHz overlaid with acoustic noise/signal interface 504 that could be caused by EMI/RFI.

When analysing an ultrasound transducer, the effect of EMI and/or RFI on a measured ultrasound acoustic signal is determined by comparing the acoustic signals when the EMI and/or RFI is mitigated and unmitigated. This comparison is used to calculate the effective attenuation of EMI and/or RFI.

As will be appreciated, when selecting a shielding material for mitigating the effects of EMI and/or RFI, the acoustic attenuation resulting from the shielding must be considered. Put another way, a shielding material must be selected that effectively attenuates EMI and/or RFI while minimally attenuating the frequency range of the acoustic signal.

Embodiments of ultrasound transducers in accordance with the subject application will now be described with reference to FIGS. 6A to 9.

Figure 6A:
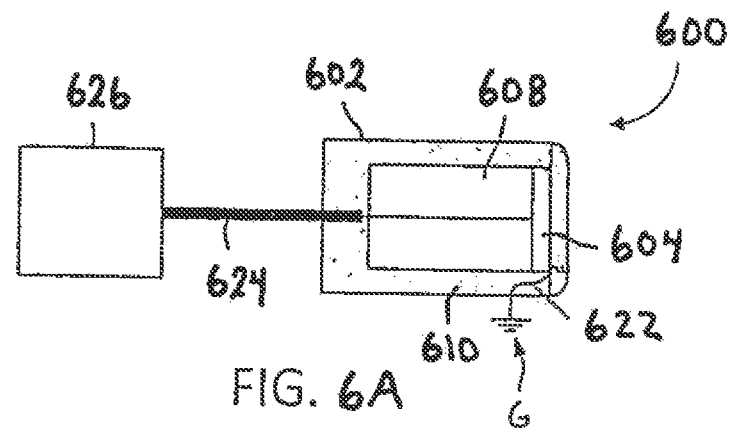
FIG. 6A is a schematic diagram of an ultrasound transducer in accordance with the subject application.
Figure 6B:
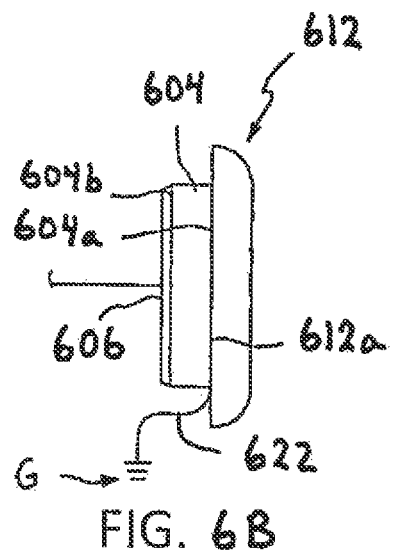
FIG. 6B is a partial side view of the ultrasound transducer of FIG. 6A.

Turning now to FIGS. 6A and 6B, an ultrasound transducer is shown and is generally identified by reference numeral 600. The ultrasound transducer 600 comprises a housing 602 formed of a metallic material that is open at one end. A piezoelectric element 604, having a front surface 604a and a rear surface 604b, is positioned within the housing 602 adjacent the open end of the housing. A potential electrode 606 overlies and covers the rear surface 604b of the piezoelectric element 604. A backing block 608 is positioned within the housing 602 behind the potential electrode 606 and the piezoelectric element 604 and acts to prevent excessive vibration of the piezoelectric element. An acoustic insulator 610 fills the void within the housing 602 and surrounds the backing block 608 and the piezoelectric, element 604 to electrically insulate the piezoelectric element from the housing 602 and to protect the piezoelectric element from transient signals. A shield 612 is suitably secured to and covers the open end of the housing 602. A cable 624 that is electrically connected to the potential electrode 606 extends from the housing 602 and is used to communicate electrical pulses to downstream equipment 626 for processing, transforming and image generation.

The shield 612, in this embodiment, is formed of elastic conductive material layer having an inner surface 612a that directly overlies the front surface 604a of the piezoelectric, element 604. The elastic conductive material layer is connected to ground G via one or more conductors or wires 622. The elastic conductive material layer comprises a matrix formed of a bulk non-electrically conductive plastic polymer having metal particles or metal ions generally uniformly dispersed. As a result, the elastic conductive material has good flexibility, elasticity and electrical characteristics. Typically, the elastic conductive material layer comprises 1% to 3% (total matrix volume) metal particles or metal ions. For example, a suitable elastic conductive material is that manufactured by NanoSonic, Inc. of Virginia U.S.A. under the name Metal Rubber™. This elastic conductive material is made in sheets having a sheet resistance in the range from 1.0Ω/☐ to 10.0Ω/☐ and a thickness of about 0.5 mm. The elastic conductive material exhibits sufficient elasticity and acoustic conductivity to enable acoustic signals to pass therethrough with minimal attenuation thereby preserving the amplitude of the acoustic signals. The elastic conductive material also exhibits sufficient electrical attenuation to reduce a 100 V/cm electric field, such as that generated during thermoacoustic imaging, to below a threshold level so that the piezoelectric element 604 is sufficiently shielded and is only exposed to low EM and/or RF emissions that do not adversely affect imaging.

During operation, when acoustic signals impinge on the ultrasound transducer 600, the acoustic signals pass through the elastic conductive material of the shield 612 with minimal attenuation and impinge on the piezoelectric element 604. In response to the force of the acoustic signals on the piezoelectric element, the piezoelectric element 604 vibrates causing the piezoelectric element to convert the vibrations into an electrical potential that appears on the potential electrode 606. In response to the electrical potential, electrical pulses are conveyed via the cable 624 to downstream equipment 626 for processing and transformation allowing the electrical pulses to be converted into a digital image. As is known, the downstream equipment comprises, one or more programmed computing devices comprising one or more processors or processing units to process and transform the electrical signals and generate a resultant digital image.

As mentioned above, the ultrasound transducer 600 may also subjected to EM and/or RF emissions during operation. The metallic material housing 602 acts as a shield to inhibit EM and/or RF emissions from entering the housing from locations other than its open end covered by the shield 612. The electrical attenuation characteristics of the shield's elastic conductive material are such that the majority of EM and/or RF emissions that impinge on the shield 612 are attenuated by the elastic conductive material before being shunted to ground G via the one or more conductors or wires 622 thereby shielding the piezoelectric element 604 from high EM and/or RF emissions. In particular, the elastic conductive material sufficiently attenuates and then shunts EM and/or RF emissions such that residual EM and/or RF emissions passing through the shield 612 expose the piezoelectric element 604 to a maximum electrical potential of 10 μV. Of course, exposing the piezoelectric element 604 to smaller electrical potentials is desired and so configuring the elastic conductive material of the shield 612 so that the piezoelectric element 604 is exposed to electrical potentials less than 10 μV, such as 5 μV or 1 μV, is preferred. As will be appreciated, the acoustic conductivity and electrical attenuation characteristics of the shield 612 can be configured to achieve the above results by changing the thickness of the elastic conductive material layer, changing the percentage of dispersed metal particles/ions in the matrix, and/or changing the bulk non-conductive material of the matrix.

Although elastic conductive material comprising a matrix formed of a bulk plastic polymer and metal particles or metal ions dispersed therein is described above, those of skill in the art will appreciate that variations are possible. For example, in other embodiments, elastic conductive materials comprising a matrix formed of other bulk non-electrically conductive polymers or rubber material having uniformly dispersed metal particles or metal ions therein comprising between 1% to 3% of a total volume of the matrix, or a fluorinated rubber material having uniformly disposed single-walled carbon nanotubes therein, may be used.

Figure 7:
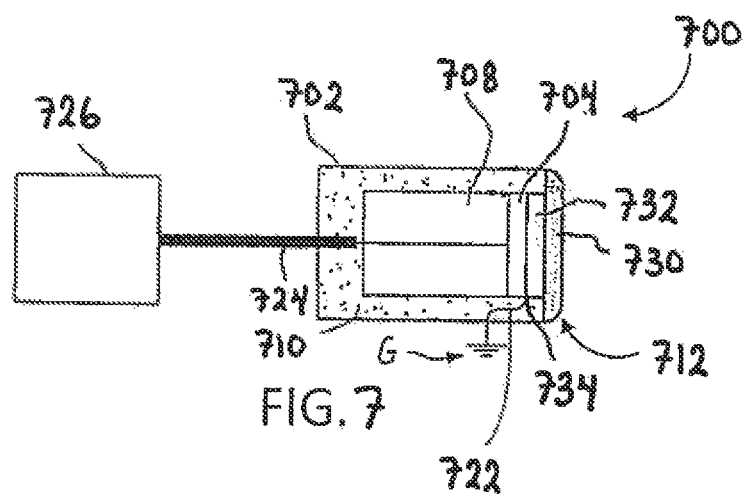
FIG. 7 is a schematic diagram of another embodiment of an ultrasound, transducer in accordance with the subject application.

Turning now to FIG. 7, another embodiment of an ultrasound transducer is shown and is generally identified by reference numeral 700. The ultrasound transducer 700 comprises a housing 702 formed of a metallic material that is open at one end. A piezoelectric element 704, having a front surface and a rear surface, is positioned within the housing 702 adjacent the open end of the housing. A potential electrode overlies and covers the rear surface of the piezoelectric element 704. A backing block 708 is positioned within the housing 702 behind the potential electrode and the piezoelectric element 704 and acts to prevent excessive vibration of the piezoelectric element. An acoustic insulator 710 fills the void within the housing 702 and surrounds the backing block 708 and the piezoelectric element 704 to electrically insulate the piezoelectric element from the housing 702 and to protect the piezoelectric element from transient signals. A shield 712 is suitably secured to and covers the open end of the housing 702. A cable 724 that is electrically connected to the potential electrode extends from the housing 702 and is used to communicate electrical pulses to downstream equipment 726 for processing, transforming and image generation.

The shield 712 in this embodiment comprises a thin membrane 730 that covers the open end of the housing 702, gel material 732 behind the thin membrane 730 and a thin ground electrode 734. The ground electrode 734 is ring-shaped and extends around the peripheral side surface(s) of the piezoelectric element 704 and surrounds the gel material 732 allowing the gel material 732 to overlie the piezoelectric element 704. The ground electrode 734 is electrically connected to ground G via one or more conductors or wires 722.

In this embodiment, the gel material 732 comprises a matrix formed of a bulk non-conductive material having conductive (metal) particles or ions generally uniformly disposed therein. As a result, the shield 712 has sufficient acoustic conductivity to enable acoustic signals to pass therethrough with minimal attenuation thereby to preserve signal amplitude. Further, the gel material 732 of the shield 712 has sufficient electrical attenuation to reduce a 100 V/cm electric field to below a threshold level so that the piezoelectric element 704 is sufficiently shielded and is only exposed to low EM and/or RF emissions that do not adversely affect imaging.

During operation, when acoustic signals impinge on the ultrasound transducer 700, the acoustic signals pass through the shield 712 with minimal attenuation and impinge on the piezoelectric element 704. In response to the force of the acoustic signals on the piezoelectric element, the piezoelectric element 704 vibrates causing the piezoelectric element to convert the vibrations, into an electrical potential that appears on the potential electrode. In response to the electrical potential, electrical pulses are conveyed, via the cable 724 to downstream equipment 726 for processing and transformation allowing the electrical pulses to be converted into a digital image.

As mentioned above, the ultrasound transducer 700 may also subjected to EM and/or RF emissions during operation. The metallic material housing 702 acts as a shield to inhibit EM and/or RF emissions from entering the housing from locations other than the open end covered by the shield 712. The electrical attenuation characteristics of the shield 712 are such that the majority of EM and/or RF emissions that impinge on the shield 712 are attenuated by the gel material 732 before being shunted to ground G via the ground electrode 734 and the one or more conductors or wires 722 thereby shielding the piezoelectric element 704 from high EM and/or RF emissions. In particular, the gel material 732 of the shield 712 sufficiently attenuates EM and/or RF, emissions such that residual EM and/or RF emissions passing through the shield 712 expose the piezoelectric element 704 to a maximum electrical potential of 10 μV. Of course, exposing the piezoelectric element 704 to smaller electrical potentials is desired and so configuring the shield 712 so that the piezoelectric element 704 is exposed to electrical potentials less than 10 μV, such as 5 μV or 1 μV, is preferred. As will be appreciated, the acoustic conductivity and electrical attenuation characteristics of the shield 712 can be configured by changing the thickness of the gel material, changing the percentage of dispersed conductive particles/ions in the matrix, and/or changing the bulk non-conductive material of the gel material.

Figure 8:
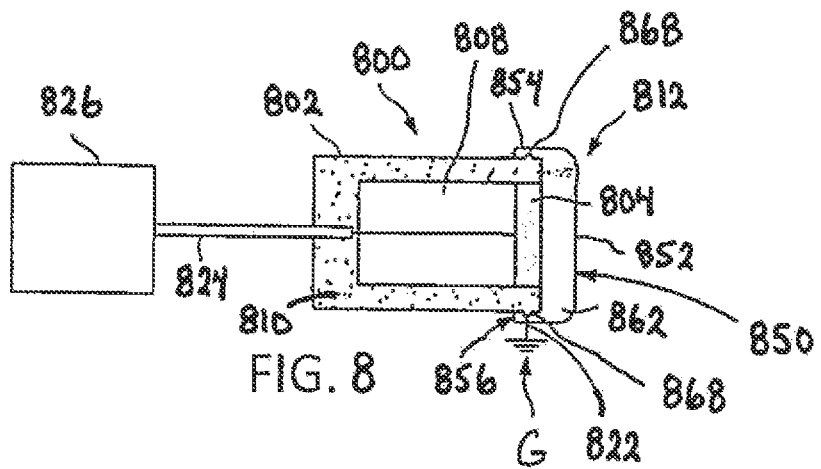
FIG. 8 is a schematic diagram of another embodiment of an ultrasound transducer in accordance with the subject application.

Turning now to FIG. 8, another embodiment of an ultrasound transducer is shown and is generally identified by reference numeral 800. The ultrasound transducer 800 comprises a housing 802 formed of a metallic material that is open at one end. A piezoelectric element 804, having a front surface and a rear surface, is positioned within the housing 802 adjacent the open end of the housing. A potential electrode overlies and covers the rear surface of the piezoelectric element 804. A backing block 808 is positioned within the housing 802 behind the potential electrode and the piezoelectric element 804 and acts to prevent excessive vibration of the piezoelectric element. An acoustic insulator 810 fills the void within the housing 802 and surrounds the backing block 808 and the piezoelectric element 804 to electrically insulate the piezoelectric element from the housing 802 and to protect the piezoelectric element from transient signals. A shield 812 covers the open end of the housing 802. A cable 824 that is electrically connected to the potential electrode extends from the housing 802 and is used to communicate electrical pulses to downstream equipment 826 for processing, transforming and image generation.

In this embodiment, the shield 812 is in the form of a cap 850 that matingly engages the open end of the housing 802 and encloses a void adjacent the open end of the housing. The cap 850 comprises a generally circular cover 852 formed of elastic material, a flexible side all 854 about the periphery of the cover 852 that extends rearwardly to, surround a portion of the housing 802, an inturned lip 856 about the distal rearward edge of the sidewall 854 that abuts the outer surface of the housing, and an upturned flange 858 about the inner distal edge of the lip 856 that runs along the outer surface of the housing 802 towards the open end of the housing. The flange 858 is configured to abut a circular protrusion or ridge 860 provided on the outer surface of the housing 802 thereby to retain the cap 850 on the open end of the housing 802. One or more conductors or wires 822 are electrically connected to the protrusion or ridge 860 and extend to ground G. In one form, the one or more conductors or wires 822 and generally flat or thin allowing them to extend between the housing 802 and the cap 850. In another form, one or more notches can be provided in the housing 802 and/or cap 850 to accommodate the one or more conductors or wires. Gel material 862 fills the void enclosed by the cap 850 so that the gel material 862 overlies the piezoelectric element 806 and contacts the housing 802.

In this embodiment, gel material comprises a matrix formed of a bulk non-conductive material having conductive (metal) particles or ions generally uniformly disposed therein. As a result, the shield 812 has sufficient acoustic conductivity to enable acoustic signals to pass therethrough with minimal attenuation thereby to preserve signal amplitude. Further, the gel material 862 of the shield 812 has sufficient electrical attenuation to reduce a 100 V/cm electric field to below a threshold level so that the piezoelectric element 804 is sufficiently shielded, and is only exposed to low EM and/or RF emissions that do not adversely affect imaging.

During operation, when acoustic signals impinge on the ultrasound transducer 800, the acoustic signals pass through the cover 852 of the cap 850 and through the gel material 862 with minimal attenuation and impinge on the piezoelectric element 804. In response to the force of the acoustic signals on the piezoelectric element, the piezoelectric element 804 vibrates causing the piezoelectric element to convert the vibrations into an electrical potential that appears on the potential electrode. In response to the electrical potential, electrical pulses are conveyed via the cable 824 to downstream equipment 826 for processing and transformation allowing the electrical pulses to be converted into a digital image.

As mentioned above, the ultrasound transducer 800 may also subjected to EM and/or RF emissions during operation. The metallic material housing 802 acts as a shield to inhibit EM and RF emissions from entering the housing from locations other than the open end covered by the shield 812. The electrical attenuation characteristics of the gel material 862 are such that the majority of EM and/or RF emissions that impinge on the shield 812 are attenuated by the gel material 862 before by being shunted to ground G via the housing 802 and the one or more conductors or wires 822 thereby shielding the piezoelectric element 804 from high EM and/or RF emissions. In particular, the gel material 862 sufficiently attenuates EM and/or RF emissions such that EM and/or RF emissions passing through the shield 812 expose the piezoelectric element 804 to a maximum electrical potential of 10 μV. Of course, exposing the piezoelectric element 804 to smaller electrical potentials is desired and so configuring the gel material 862 so that the piezoelectric element 804 is exposed to electrical potentials less than 10 μV, such as 5 μV or 1 μV, is preferred. As will be appreciated, the acoustic conductivity and electrical attenuation characteristics of the shield 812 can be configured by changing the thickness of the gel material, changing the percentage of dispersed conductive particles/ions in the matrix, and/or changing the bulk non-conductive material of the gel material.

Those of skill in the art will appreciate that the connection of the cap 850 to the open end of the housing 802 allows the cap to be removed from the housing. This of course allows the cap 850 to be connected to the housing 802 of the ultrasound, transducer 800 on site. In this case, prior to connection of the cap 850 to the open end of the housing 802, a suitable amount of gel material 862 is placed within the cap 850 and/or on the piezoelectric element 806 and then the cap 850 is pushed onto the open end of the housing 802 until the flange 858 rides over the circular protrusion or ridge 860 and snap fits behind the circular protrusion or ridge 860. Any excess gel material trapped within the void enclosed by the cap 850 is squeezed and forced out of the ultrasound transducer 800 beyond the interned lip 856.

In the embodiments described above, although a cable is used to convey electrical signals to the downstream equipment in response to the electrical potential appearing on the potential electrode, those of skill in the art will appreciate that alternative communication links may be used. For example, alternative wired links may be used or wireless communication links (e.g. Wifi, Bluetooth etc.) may be employed to convey electrical signals from the ultrasound transducers to the downstream equipment.

Although exemplary ultrasound transducers have been described above with reference to FIGS. 6A to 8, those of skill in the art will appreciate that variations are possible. For example, if desired rather than using the shields to attenuate and shunt the majority of EM and/or RF emissions to ground to inhibit exposure of the piezoelectric elements to electric fields of magnitudes that may adversely affect imaging, the one or more conductors or wires connected to ground may be removed and the housings of the ultrasound transducers within the ultrasound probes may be surrounded by Faraday cage-like structures to shield the ultrasound transducers from EM and/or RF emissions. Residual EM and/or RF emissions passing through the faraday cage-like structures are then further attenuated by the shields thereby further reducing the magnitude of any electric potential to which the piezoelectric elements are exposed.

Figure 9:
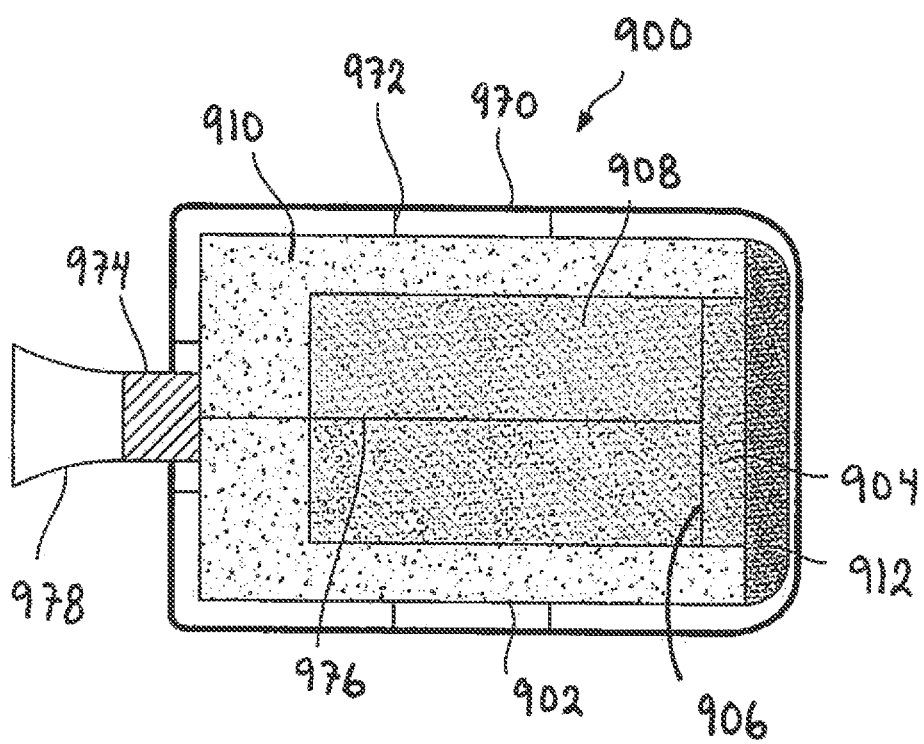
FIG. 9 is a schematic diagram of another embodiment of an ultrasound transducer is accordance with the subject application.

For example, turning now to FIG. 9, another embodiment of an ultrasound transducer is shown and is generally identified, by reference numeral 900. The ultrasound transducer 900 comprises a generally cylindrical housing 902 formed of a suitable metallic or non-metallic material that is open at one end. A piezoelectric 904 element having a front surface and a rear surface is positioned within the housing 902 adjacent the open end of the housing. A potential electrode 906 overlies and covers the rear surface of the piezoelectric element 904. A backing block 908 is positioned within the housing 902 behind the potential electrode 906 and the piezoelectric element 904 and acts to prevent excessive vibration of the piezoelectric element. An acoustic insulator 910 fills the void within the housing 902 and surrounds the backing block 908 and the piezoelectric element 904 to electrically insulate the piezoelectric element from the housing and to protect the piezoelectric element 904 from transient signals. A shield 912 covers the open end of the housing 902.

A cage-like structure 970 formed of electrically conductive material and in the form of a screen or mesh surrounds the housing 902 and the shield 912. Electrical insulators 972 extend between the housing 902 and the cage-like structure 970 at spaced locations to maintain a gap between the housing 902 and shield 912 and the cage-like structure 970. The cage-like structure 970 relies on the Faraday effect to enable acoustic, signals to propagate therethrough but inhibit electromagnetic interference (EMI) and/or radio frequency interference (RFI) from passing therethrough. The cage-like structure 970 is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than 10 µV. Of course, exposing the piezoelectric element 904 to smaller electrical potentials, such as 5 µV or 1 µV, is preferred.

In this embodiment, as the cage-like structure 970 surrounding the housing 902 and shield 912 is configured to inhibit significant EMI and/or RFI from impinging on the shield 912, the shield can be formed of any suitable material having good acoustic conductivity characteristics. Of course, shields similar in design to those shown in FIGS. 6A to 8 may be employed.

An acoustic coupler 974 that extends from the rear of the housing 902 and passes through the cage-like structure 970 is electrically connected to the potential electrode 906 via a conductor 976 and communicates with a wireless transmitter 978 to allow electrical signals to be communicated to downstream equipment for processing, transformation and image generation.

During operation, when acoustic signals pass through the cage-like structure 970 and impinge on the ultrasound transducer 800, the acoustic signals pass through the shield 912 with minimal attenuation and impinge on the piezoelectric element 904. In response to the force of the acoustic signals on the piezoelectric element, the piezoelectric element 904 vibrates causing the piezoelectric element to convert the vibrations into an electrical potential that appears on the potential electrode. In response to the electrical potential, electrical pulses are conveyed via conductor 976 to the acoustic couple 974. The acoustic coupler 974 in turn provides the electrical signals to the wireless transmitter 978 for wireless transmission to the downstream equipment for processing and transformation allowing, the electrical pulses to be converted into a digital image.

As mentioned above, the ultrasound transducer 900 may also subjected to EM and/or RF emissions during operation. The cage-like structure acts as a shield to inhibit EM and RF emissions from passing therethrough and impinging on the housing 902 and/or shield 912. In particular, the cage-like structure 970 sufficiently attenuates EM and/or RF emissions such that EM and/or RF emissions passing therethrough expose the piezoelectric element 804 to a maximum electrical potential of 10 µV.

In the above embodiment, although the cage-like structure 970 is described and shown as being spaced from the housing and shield, those of skill in the art will appreciate the cage-like structure 970 may be configured to envelope the housing 902 and shield 912 so that little or no gap between the cage-like structure 970 and housing/shield exists.

Although the ultrasound transducers described above and illustrated in the drawings are depicted as comprising a single piezoelectric element, those of skill in the art will appreciate that the ultrasound transducer may comprise an array of piezoelectric elements that are suitably shielded from EMI and/or RFI by the shields or cage-like structure.

Figure 10:
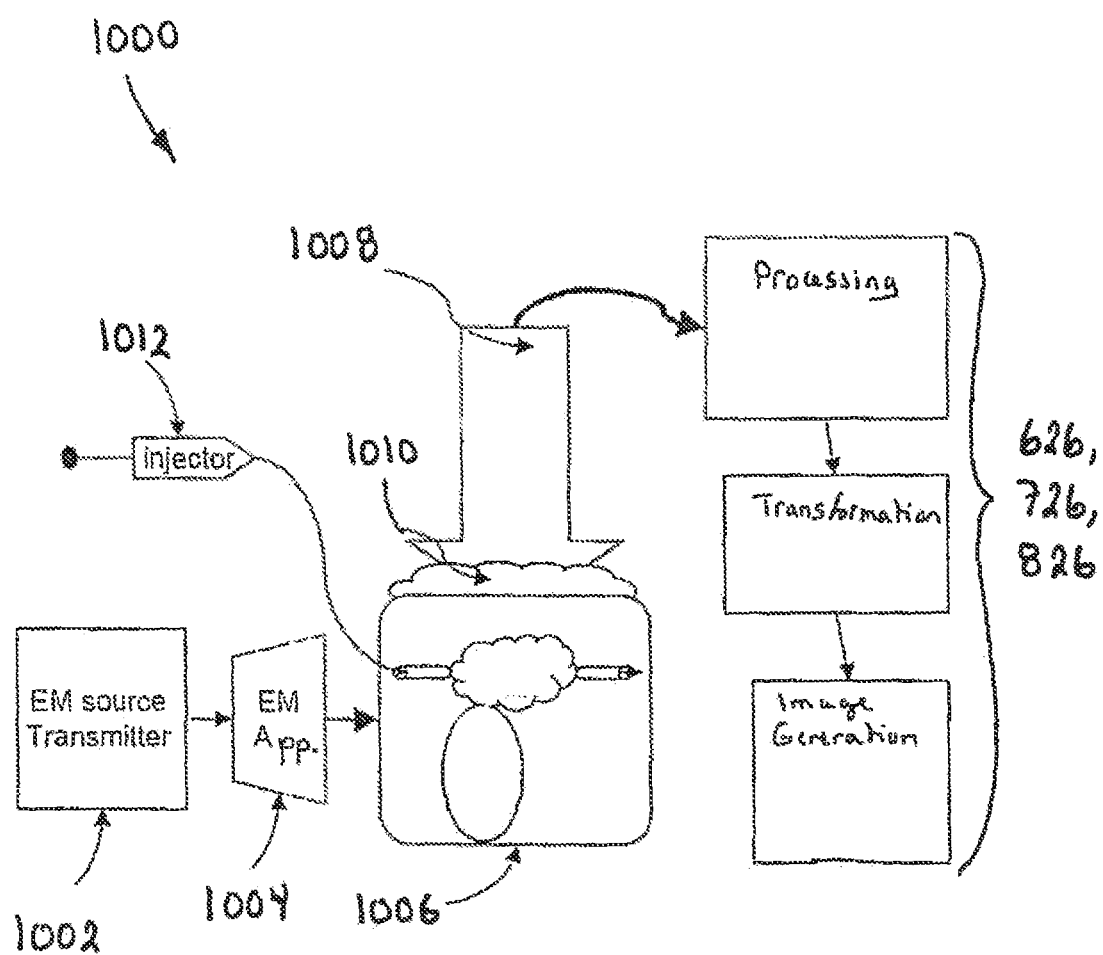
FIG. 10 is a block diagram of a thermoacoustic imaging system employing an ultrasound transducer in accordance with the subject application.

Turning now to FIG. 10, a thermoacoustic imaging system is shown and is generally identified by reference character 1000. As can be seen, the thermoacoustic imaging system 1000 comprises an EM transmitter or power source 1002 configured to supply energy at the appropriate power, frequency and pulse shape to an EM applicator 1004. The EM applicator 1004, which is positioned in close proximity to a subject 1006 being imaged to ensure good energy coupling, transmits high energy RF pulses into the subject 1006. The high energy RF pulses transmitted into the subject 1006 stimulate the generation of thermoacoustic signals. An ultrasound probe 1008 is coupled with the subject via an acoustic coupling liquid or gel 1010. In this embodiment, the ultrasound probe 1008 comprises one of the ultrasound transducers 600, 700, 800, or 900 described above encased in a plastic housing to shield the piezoelectric element(s) of the ultrasound probe from the significant electric field generated as a result of the high energy RF pulses. In response to thermoacoustic signals generated within the subject 1006 that are returned to ultrasound probe, the ultrasound probe 1008 outputs electrical pulses via a suitable wired or wireless link (e.g. cable 624, 724, 824 or wireless transmitter 978) to downstream equipment 626, 726, 826 for processing, transforming and image generation. An injector 1012 that can, be manually or motor controlled injects a suitable contrast agent into the subject 1006.

The EM transmitter or energy source 1002 in this embodiment is chosen 1) to provide a penetration depth in tissue suitable for a specific application, 2) to permit generation of individual pulses with a rise time short enough to produce acoustic pulses with detectable energy above 1 MHz, and 3) to allow absorption to provide contrast. At least three specific regions of the EM spectrum are useful for this purpose: 1) near infrared light between 600 nm and 1000 nm, which has a useful penetration depth up to 2 cm; 2) microwave energy between 1 GHz and 10 GHz, which exhibits good tissue contrast and penetration depth up to several centimeters; and 3) very high frequency and ultrahigh frequency radio waves between 26 MHz and 1000 MHz, which have frequencies high enough to produce the required short pulse rise time, and penetration depth of greater than several cm.

Although the ultrasound transducers are described above as being used in a thermoacoustic imaging system with reference to FIG. 10, those of skill in the art will appreciate that the ultrasound transducers are well suited for use in other types of ultrasound imaging systems, especially those employed in high EM and/or RF emission environments.

Other aspects of ultrasound transducers according to the subject application are exemplified in the following clauses:

A1. An ultrasound transducer comprising:
at least one piezoelectric element configured to convert received acoustic signals into an electric potential;
a shield overlying the at least one piezoelectric element through which the acoustic signals pass before being received by the at least one piezoelectric element, the shield having acoustic conductivity and electrical attenuation characteristics that enable the acoustic signals to propagate therethrough while attenuating electromagnetic interference (EMI) and/or radio frequency interference (RFI) to below a threshold level, the shield comprising a bulk non-electrically conductive material and being connectable to ground via one or more conductors; and a housing accommodating the at least one piezoelectric element and shield.

A2. The ultrasound transducer of clause A1, wherein the bulk non-electrically conductive material is a polymer material or rubber material.

A3. The ultrasound transducer of clause A2, wherein the polymer material or rubber material has metal particles or metal ions generally uniformly dispersed therein.

A4. The ultrasound transducer of clause A1, wherein said shield is formed of an elastic conductive material, the elastic conductive material comprising a matrix formed, of a bulk plastic polymer with metal particles or metal ions generally uniformly dispersed therein.

A5. The ultrasound transducer of any one of clauses A1 to A4, wherein the metal particles or metal ions comprise 1% to 3% total volume of the shield.

A6. The ultrasound transducer of clause A2, wherein the rubber material is a fluorinated rubber material having uniformly disposed single-walled carbon nanotubes therein.

A7. The ultrasound transducer of any one of clauses A1 to A6, further comprising one or more conductors electrically connecting the shield to ground.

A8. The ultrasound transducer of clause A1, wherein the bulk non-electrically conductive material is a gel material.

A9. The ultrasound transducer of clause A8, wherein said shield further comprises a membrane overlying an open end of said housing and wherein said gel material is interposed between said membrane and said at least one piezoelectric element.

A10. The ultrasound transducer of clause A9, wherein said shield further comprises a ground electrode adjacent a peripheral side surface of said, at least one piezoelectric element, said ground electrode being electrically coupled to said gel material and to ground via at least one conductor.

A11. The ultrasound transducer of clause A8, wherein said shield comprises a cap on an open end of said housing enclosing a void within which said gel material is accommodated.

A12. The ultrasound transducer of clause A11, wherein said cap matingly engages the open end of said housing.

A13. The ultrasound transducer of clause A12, wherein said cap comprises an elastic cover, a sidewall about the periphery of the cover that extends rearwardly to surround a portion of the housing, an inturned lip about the distal rearward edge of the sidewall that abuts an outer surface of the housing, and an upturned flange about the inner distal edge of the lip that runs along the outer surface of the housing towards the open end of the housing, wherein the upturned flange and housing outer surface carry mating formations and wherein the housing is electrically coupled with the gel material and electrically grounded adjacent said cap via at least one conductor.

B1. An ultrasound transducer comprising:

at least one piezoelectric element configured to convert received acoustic signals into an electric potential;

a shield connectable to ground and overlying the at least one piezoelectric element through which the acoustic signals pass before being received by the at least one piezoelectric element, the shield having acoustic conductivity and electrical attenuation characteristics that enable the acoustic signals to propagate therethrough while reducing a 100 volt per centimeter electric field to below a threshold level so that the piezoelectric element is exposed to a threshold electrical potential at least less than or equal to 10 µV; and a housing accommodating the at least one piezoelectric element and shield.

B2. The ultrasound transducer of clause B1, wherein the threshold electrical potential is less than or equal to 5 µV.

B3. The ultrasound transducer of clause B1, wherein the threshold electrical potential is less than or equal to 1 µV.

B4. The ultrasound transducer of any one of clauses B1 to B3, wherein said shield is formed of an elastic conductive material, the elastic conductive material comprising a matrix formed of a bulk polymer material with metal particles or metal ions generally uniformly dispersed therein.

B5. The ultrasound transducer of clause B4, wherein the metal particles or metal ions comprise 1% to 3% total volume of the shield.

B6. The ultrasound transducer of any one of clauses B1 to B5, further comprising one or more conductors electrically connecting said shield to ground.

B7. The ultrasound transducer of any one of clauses B1 to B3, wherein said shield comprises a membrane overlying an open end of said housing and gel material interposed between said elastic membrane and said at least one piezoelectric element.

B8. The ultrasound transducer of clause B7, wherein said shield further comprises a ground electrode adjacent a peripheral side surface of said at least one piezoelectric element, said ground electrode being electrically coupled to said gel material and to ground via at least one conductor.

B9. The ultrasound transducer of any one of clauses B1 to B3, wherein said shield comprises a cap on an open end of said housing enclosing a void and gel material accommodated by said void.

B10. The ultrasound transducer of clause B9, wherein said cap comprises an elastic cover, a sidewall about the periphery of the cover that extends rearwardly to surround a portion of the housing, an inturned lip about the distal rearward edge of the sidewall that abuts an outer surface of the housing, and an upturned flange about the inner distal edge of the lip that runs along the outer surface of the housing towards the open end of the housing, wherein the upturned flange and housing outer surface carry mating formations and wherein the housing is electrically coupled to said gel material and is electrically grounded adjacent said cap via at least one conductor.

C1. An ultrasound medical or thermoacoustic imaging system comprising an ultrasound probe having the ultrasound transducer of any one of clauses A1 to A13 therein.

D1. An ultrasound medical or thermoacoustic imaging system comprising an ultrasound probe having the ultrasound transducer of any one of clauses B1 to B10 therein.

E1. An ultrasound transducer comprising at least one piezoelectric element configured to convert received acoustic signals into an electric potential; a shield overlying the at least one piezoelectric element through which the acoustic signals pass before being received by the at least one piezoelectric element, the shield being formed of an elastic conductive material, having acoustic conductivity and electrical attenuation characteristics that enable the acoustic signals to propagate therethrough while attenuating electromagnetic interference (EMI) and/or radio frequency interference (RFI) to below a threshold level; and a housing accommodating the at least one piezoelectric element and shield.

E2. The ultrasound transducer of clause E1, wherein said elastic conductive material comprises a matrix formed of a bulk polymer material with metal particles or metal ions generally uniformly dispersed therein.

E3. The ultrasound transducer of clause E2, wherein the metal particles or metal ions comprise 1% to 3% total volume of the shield.

E4. The ultrasound transducer of any one of clauses E1 to E3, wherein said shield is electrically grounded via at least one conductor.

E5. The ultrasound transducer of any one of clauses E1 to E4, wherein the electrical attenuation characteristics of the shield reduce a 100 volt per centimeter electric field to below a threshold level so that the piezoelectric element is exposed to an electrical potential less than or equal to 10 µV.

E6. The ultrasound transducer of any one of clauses E1 to E4, wherein the electrical attenuation characteristics of the shield reduce a 100 volt per centimeter electric field to below a threshold level so that the piezoelectric element is exposed to an electrical potential less than or equal to 5 µV.

E7. The ultrasound transducer of any one of clauses E1 to E4, wherein the electrical, attenuation characteristics of the shield reduce a 100 volt per centimeter electric field to below a threshold level so that the piezoelectric element is exposed to an electrical potential less than or equal to 1 µV.

F1. An ultrasound transducer comprising at least one piezoelectric element configured to convert received acoustic signals into an electric potential; a shield overlying the at least one piezoelectric element through which the acoustic signals pass before being received by the at least one piezoelectric element; and a housing accommodating the at least one piezoelectric element and the shield, wherein the shield comprises a membrane overlying an open end of said housing, gel material interposed between said membrane and said at least, one piezoelectric element, and a ground electrode adjacent a peripheral side surface of said at least one piezoelectric element, said ground electrode being electrically coupled to said gel material and to ground via at least one conductor, and wherein the shield has acoustic conductivity and electrical attenuation characteristics that enable the acoustic signals to propagate therethrough while attenuating electromagnetic interference (EMI) and/or radio frequency interference (RFI) to below a threshold level.

F2. The ultrasound transducer of clause F1, wherein the electrical attenuation characteristics of the shield reduce a 100 volt per centimeter electric field to below a threshold level so that the piezoelectric element is exposed to an electrical potential less than or equal to 10 µV.

F3. The ultrasound transducer of clause F1, wherein the electrical attenuation characteristics of the shield reduce a 100 volt per centimeter electric field to below a threshold level so that the piezoelectric element is exposed to an electrical potential less than or equal to 5 µV.

F4. The ultrasound transducer of clause F1, wherein the electrical attenuation characteristics of the shield reduce a 100 volt per centimeter electric field to below a threshold level so that the piezoelectric element is exposed to an electrical potential less, than or equal to 1 µV.

G1. An ultrasound transducer comprising at least one piezoelectric element configured to convert received acoustic signals into an electric potential; a shield overlying the at least one piezoelectric element through which the acoustic signals pass before being received by the at least one piezoelectric element; and a housing accommodating the at least one piezoelectric element and the shield, wherein the shield is in the form of a cap covering an open end of said housing, said cap comprising an elastic cover, a sidewall about the periphery of the cover that extends rearwardly to surround a portion of the housing, an inturned lip about the distal rearward edge of the sidewall that abuts an outer surface of the housing, and an upturned flange about the inner distal edge of the lip that runs along the outer surface of the housing towards the open end of the housing, wherein the upturned flange and housing outer surface carry mating formations and wherein the housing is electrically coupled to said gel material and is electrically grounded adjacent said cap via at least one conductor, and wherein the shield has acoustic conductivity and electrical attenuation characteristics that enable the acoustic signals to propagate therethrough while attenuating electromagnetic interference (EMI) and/or radio frequency interference (RFI) to below a threshold level.

G2. The ultrasound transducer of clause G1, wherein the electrical attenuation characteristics of the shield reduce a 100 volt per centimeter electric field to below a threshold level so that the piezoelectric element is exposed to an electrical potential less than, or equal to 10 µV.

G3. The ultrasound transducer of clause G1, wherein the electrical attenuation characteristics of the shield reduce a 100 volt per centimeter electric field to below a threshold level so that the piezoelectric element is exposed to an electrical potential less than or equal to 5 µV.

G4. The ultrasound transducer of clause G1, wherein the electrical attenuation characteristics of the shield reduce a 100 volt per centimeter electric field to below a threshold level so that the piezoelectric element is exposed to an electrical potential less than or equal to 1 µV.

H1. An ultrasound transducer comprising:
at least one piezoelectric element configured to convert received acoustic signals into an electric potential;
a housing accommodating the at least one piezoelectric element;
a cover on an end of the housing and overlying the at least one piezoelectric element through which the acoustic signals pass before being received by the at least one piezoelectric element; and
a cage-like structure formed of electrically conductive material surrounding the housing, the cage-like structure configured to enable the acoustic signals to propagate therethrough and configured to inhibit electromagnetic interference (EMI) and/or radio frequency interference (RFI) from passing therethrough.

H2. The ultrasound transducer of clause H1, wherein the cage-like structure is electrically insulated from the housing by one or more insulators extending between the cage-like structure and the housing.

H3. The ultrasound transducer of clause H2, wherein the cage-like structure is a faraday cage.

H4. The ultrasound transducer of any one of clauses H1 to H3, wherein said cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 10 µV.

H5. The ultrasound transducer of any one of clauses H1 to H3, wherein said cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 5 µV.

H6. The ultrasound transducer of any one of clauses H1 to H3, wherein said cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 1 µV.

I1. An ultrasound transducer comprising:
at least one piezoelectric element configured to convert received acoustic signals into an electric potential;
a housing accommodating the at least one piezoelectric element;
a cover on an end of the housing and overlying the at least one piezoelectric element through which the acoustic signals pass before being received by the at least one piezoelectric element; and
a cage-like structure formed of electrically conductive material surrounding the housing, wherein said cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential at least less than or equal to 10 µV.

I2. The ultrasound transducer of clause I1, wherein the electrical attenuation characteristics of the shield reduce the 100 volt per centimeter electric field so that the piezoelectric element is exposed to an electrical potential less than or equal to 5 µV.

I3. The ultrasound transducer of clause I1, wherein the electrical attenuation characteristics of the shield reduce the 100 volt per centimeter electric field so that the piezoelectric element is exposed to an electrical potential less than or equal to 1 µV.

J1. An ultrasound medical or thermoacoustic imaging system comprising an ultrasound probe having the ultrasound transducer of any one of clauses E1 to E7, F1 to F4, G1 to G4, H1 to H6 or I1 to I3 therein.

Although embodiments have been described above with reference to the accompanying drawings, those of skill in the art will appreciate that variations and modifications may be made without departing from the scope thereof as defined by the appended claims.

What is claimed is:

1. An ultrasound transducer comprising:
at least one piezoelectric element configured to convert received acoustic signals into an electric potential;
a shield connectable to ground and overlying the at least one piezoelectric element through which the acoustic signals pass before being received by the at least one piezoelectric element, the shield having acoustic conductivity and electrical attenuation characteristics that enable the acoustic signals to propagate therethrough while reducing a 100 volt per centimeter electric field to below a threshold level so that the piezoelectric element is exposed to a threshold electrical potential at least less than or equal to 10 µV; and
a housing accommodating the at least one piezoelectric element and shield.

2. The ultrasound transducer of claim 1, wherein the threshold electrical potential is less than or equal to 5 µV.

3. The ultrasound transducer of claim 1, wherein the threshold electrical potential is less than or equal to 1 µV.

4. The ultrasound transducer of claim 1, wherein said shield is formed of an elastic conductive material, the elastic conductive material comprising a matrix formed of a bulk polymer material with metal particles or metal ions generally uniformly dispersed therein.

5. The ultrasound transducer of claim 4, wherein the metal particles or metal ions comprise 1% to 3% total volume of the shield.

6. The ultrasound transducer of claim 1, further comprising one or more conductors electrically connecting said shield to ground.

7. The ultrasound transducer of claim 1, wherein said shield comprises a membrane overlying an open end of said housing and gel material interposed between said membrane and said at least one piezoelectric element.

8. The ultrasound transducer of claim 7, wherein said shield further comprises a ground electrode adjacent a peripheral side surface of said at least one piezoelectric element, said ground electrode being electrically coupled to said gel material and to ground via at least one conductor.

9. The ultrasound transducer of claim 1, wherein said shield comprises a cap on an open end of said housing enclosing a void and gel material accommodated by said void.

10. The ultrasound transducer of claim 9, wherein said cap comprises an elastic cover, a sidewall about the periphery of the cover that extends rearwardly to surround a portion of the housing, an inturned lip about the distal rearward edge of the sidewall that abuts an outer surface of the housing, and an upturned flange about the inner distal edge of the lip that runs along the outer surface of the housing towards the open end of the housing, wherein the upturned flange and housing outer surface carry mating formations and wherein the housing is electrically coupled to said gel material and is electrically grounded adjacent said cap via at least one conductor.

11. An ultrasound transducer comprising:
at least one piezoelectric element configured to convert received acoustic signals into an electric potential;
a housing accommodating the at least one piezoelectric element;
a cover on an end of the housing and overlying the at least one piezoelectric element through which the acoustic signals pass before being received by the at least one piezoelectric element; and
a cage-like structure formed of electrically conductive material surrounding the housing, the cage-like structure configured to enable the acoustic signals to propagate therethrough and configured to inhibit electromagnetic interference (EMI) and/or radio frequency interference (RFI) from passing therethrough.

12. The ultrasound transducer of claim 11, wherein the cage-like structure is electrically insulated from the housing by one or more insulators extending between the cage-like structure and the housing.

13. The ultrasound transducer of claim 12, wherein the cage-like structure is a faraday cage.

14. The ultrasound transducer of claim 12, wherein said cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 10 µV.

15. The ultrasound transducer of claim 12, wherein said cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 5 µV.

16. The ultrasound transducer of claim 12, wherein said cage-like structure is configured to inhibit electromagnetic interference (EMI) and/or radio frequency interference (RFI) from passing therethrough such that exposure of the ultrasound transducer to a 100 volt per centimeter electric field results in the piezoelectric element being exposed to an electrical potential less than or equal to 1 µV.

\* \* \* \* \*